United States Patent [19]

Wilk

[11] Patent Number: 5,267,554
[45] Date of Patent: Dec. 7, 1993

[54] SPREADABLE LAPAROSCOPIC RETRACTOR AND ASSOCIATED METHOD OF USE

[76] Inventor: Peter J. Wilk, 185 W. End Ave., New York, N.Y. 10023

[21] Appl. No.: 833,510

[22] Filed: Feb. 11, 1992

Related U.S. Application Data

[63] Continuation-in-part of Ser. No. 792,379, Nov. 15, 1991, Pat. No. 5,152,279.

[51] Int. Cl.⁵ .................... A61B 17/02; A61B 1/32
[52] U.S. Cl. ............................. 128/20; 128/17; 606/198
[58] Field of Search ............... 128/17, 20, 3, 18, 19; 606/191, 198; 604/104–109

[56] References Cited

U.S. PATENT DOCUMENTS

| | | |
|---|---|---|
| 817,973 | 4/1906 | Hausmann . |
| 3,517,128 | 6/1970 | Hines . |
| 3,744,481 | 7/1973 | McDonald . |
| 3,810,462 | 5/1974 | Szpur . |
| 4,350,151 | 9/1982 | Scott . |
| 4,702,230 | 10/1987 | Pelta . |
| 4,726,356 | 2/1988 | Santilli et al. . |
| 4,909,789 | 3/1990 | Taguchi et al. ............ 604/107 |
| 4,966,130 | 10/1990 | Montaldi . |
| 5,052,373 | 10/1991 | Michelson . |
| 5,152,279 | 10/1992 | Wilk ........................... 128/20 |
| 5,176,128 | 1/1993 | Andrese ...................... 128/20 |
| 5,178,133 | 1/1993 | Pena ........................... 606/198 |

FOREIGN PATENT DOCUMENTS

| | | | |
|---|---|---|---|
| 632341 | 11/1978 | U.S.S.R. | 128/17 |
| 736949 | 5/1980 | U.S.S.R. | 606/198 |
| 1577769 | 7/1990 | U.S.S.R. | 128/20 |
| 143802 | 6/1920 | United Kingdom | 604/106 |

Primary Examiner—Richard J. Apley
Assistant Examiner—Donna L. Maraglio
Attorney, Agent, or Firm—R. Neil Sudol; Henry D. Coleman

[57] ABSTRACT

A retractor instrument for use in laparoscopic surgery, comprises an elongate frame or holder and a substantially rigid retractor member movably mounted to the frame. A first retainer component is mounted to frame for maintaining the retractor member in substantially parallel relation to the frame during an insertion of the retractor instrument through a patient's abdominal wall and partially into the patient's abdominal cavity in a laparoscopic procedure. A second retainer component is connected to the frame for maintaining the retractor member in an angled orientation with respect to the frame during utilization of the retractor instrument to displace an internal body organ of the patient in the laparoscopic procedure.

11 Claims, 8 Drawing Sheets

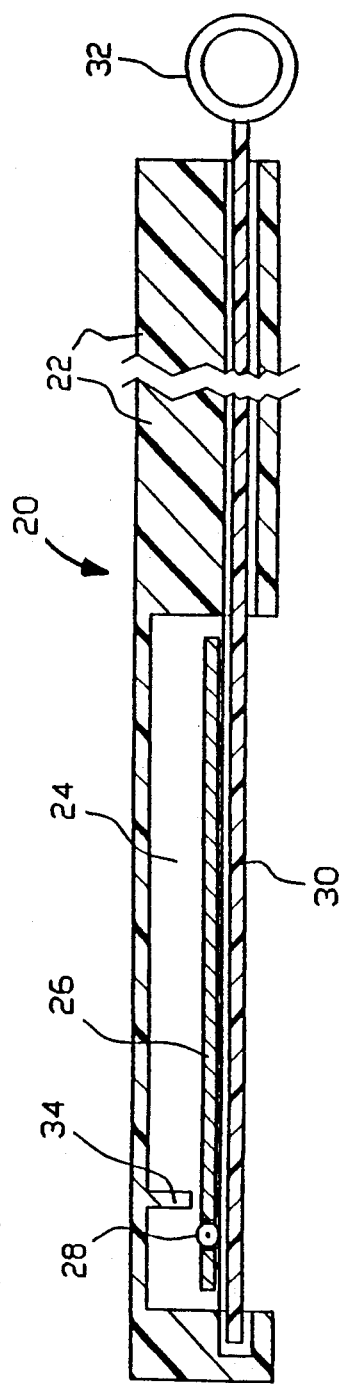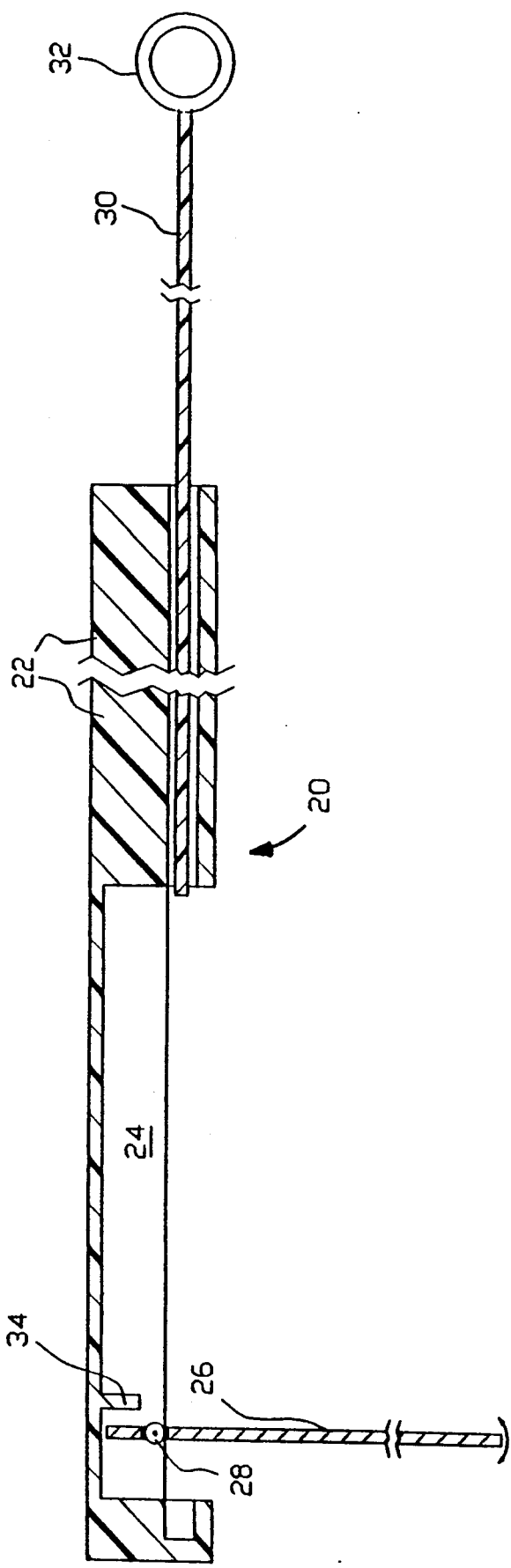

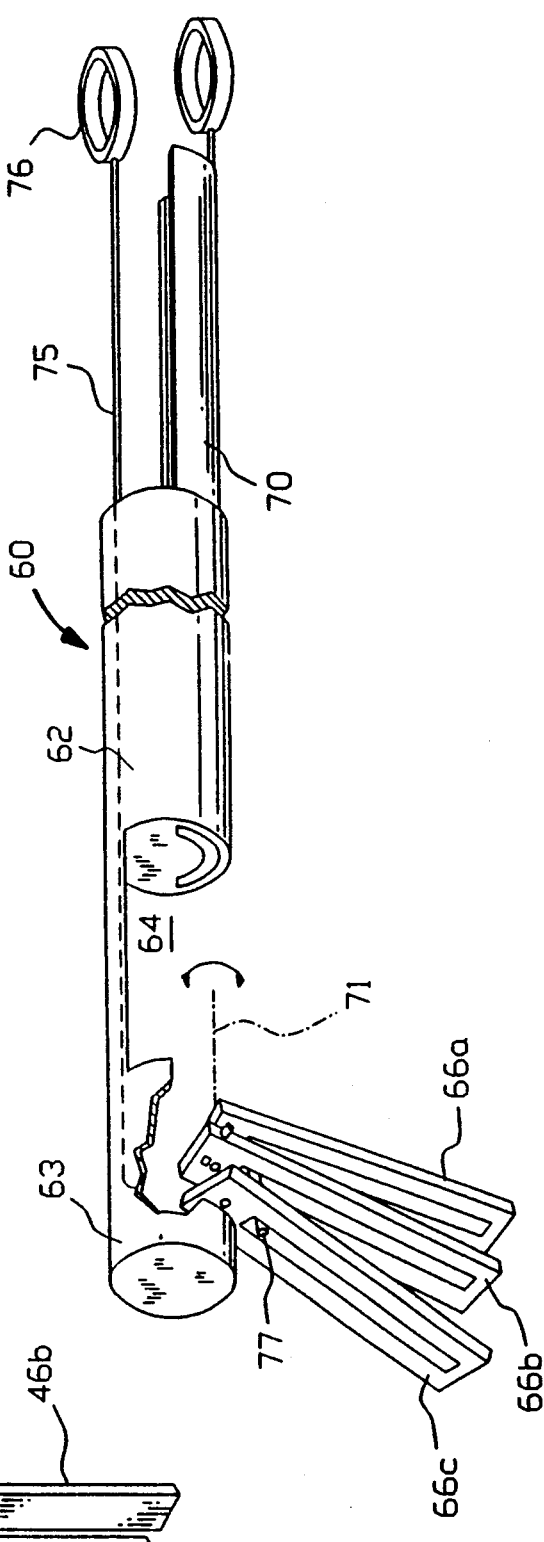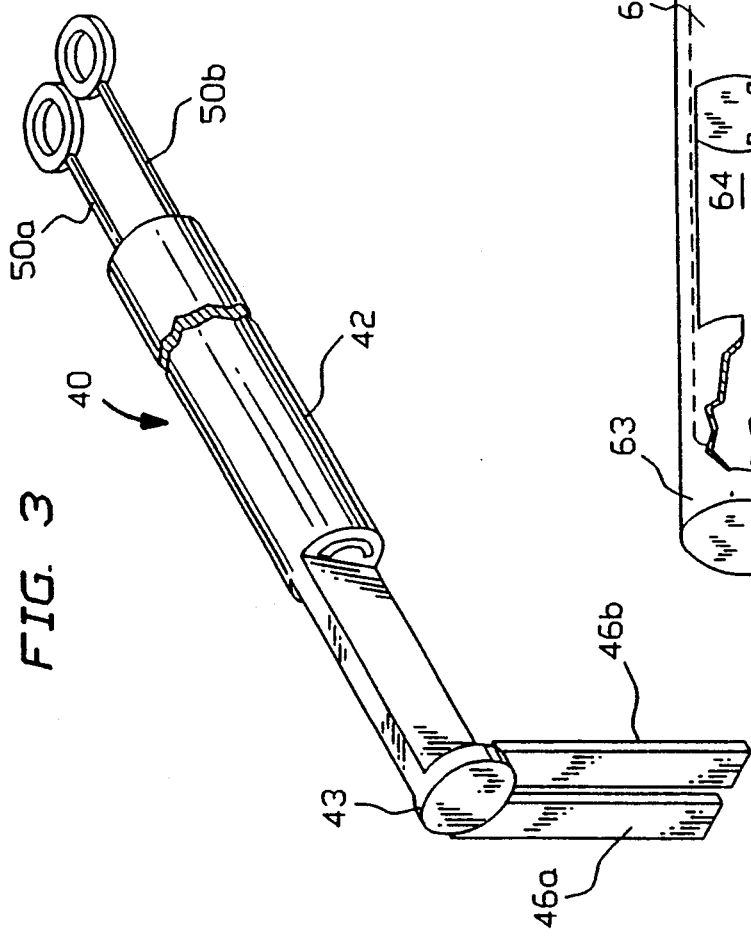

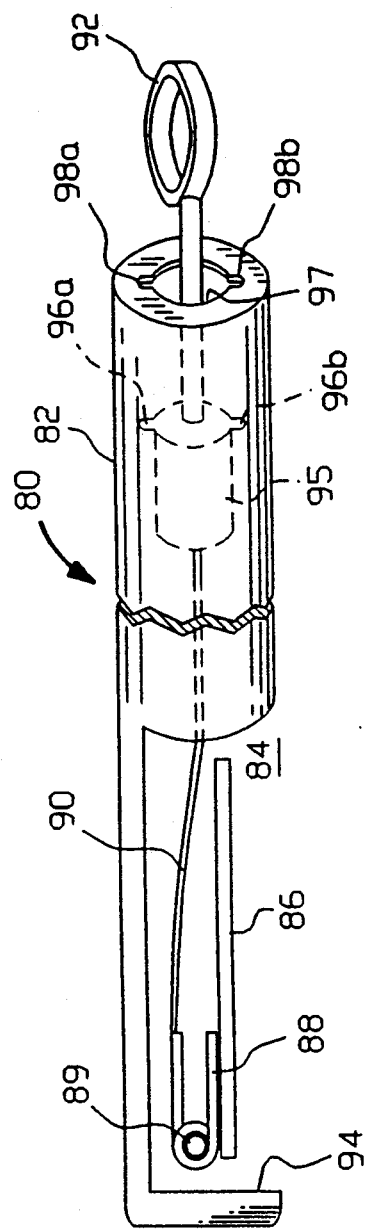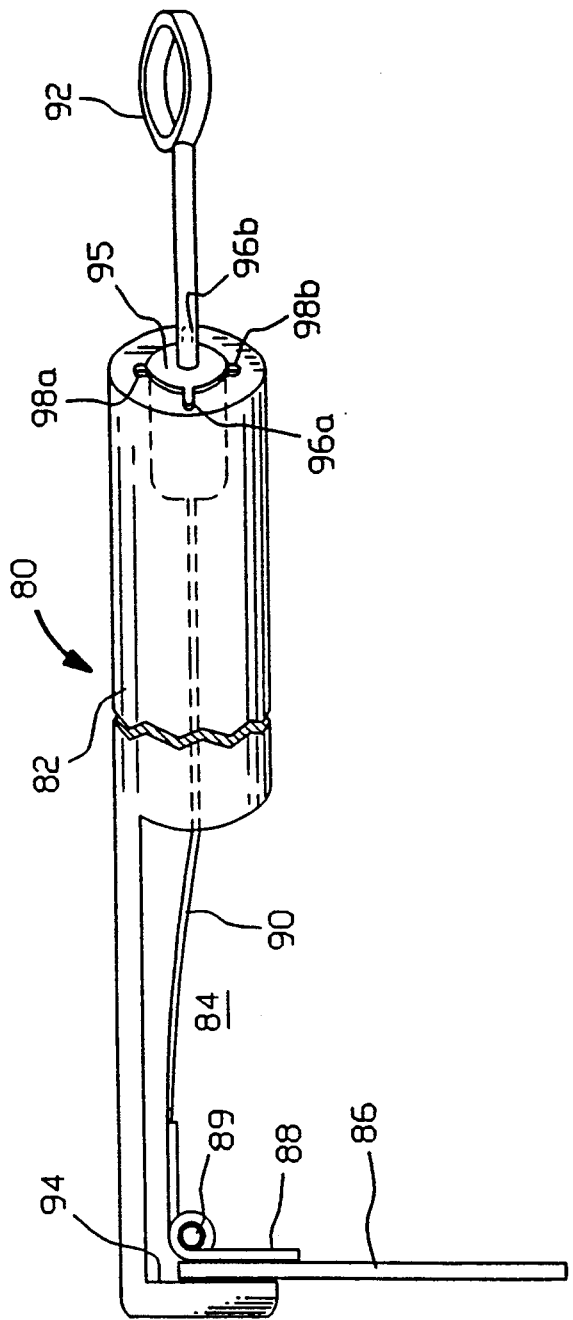

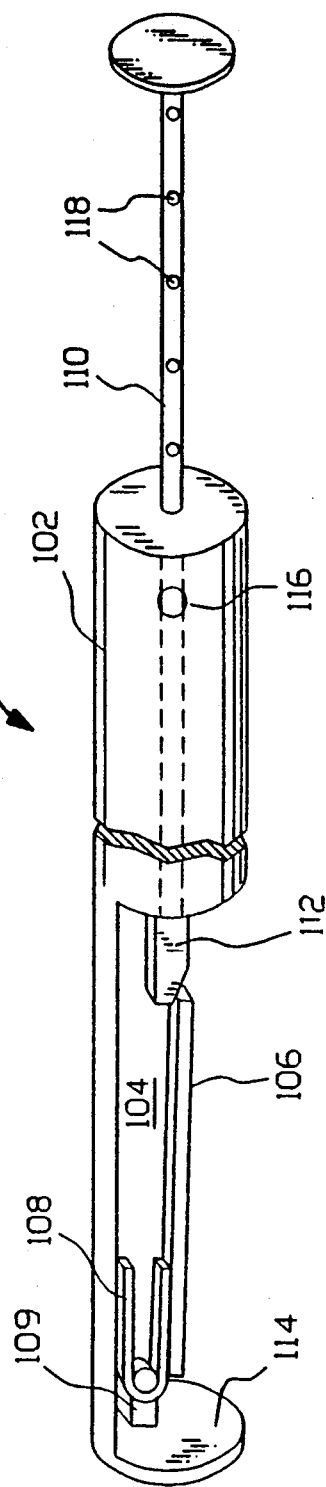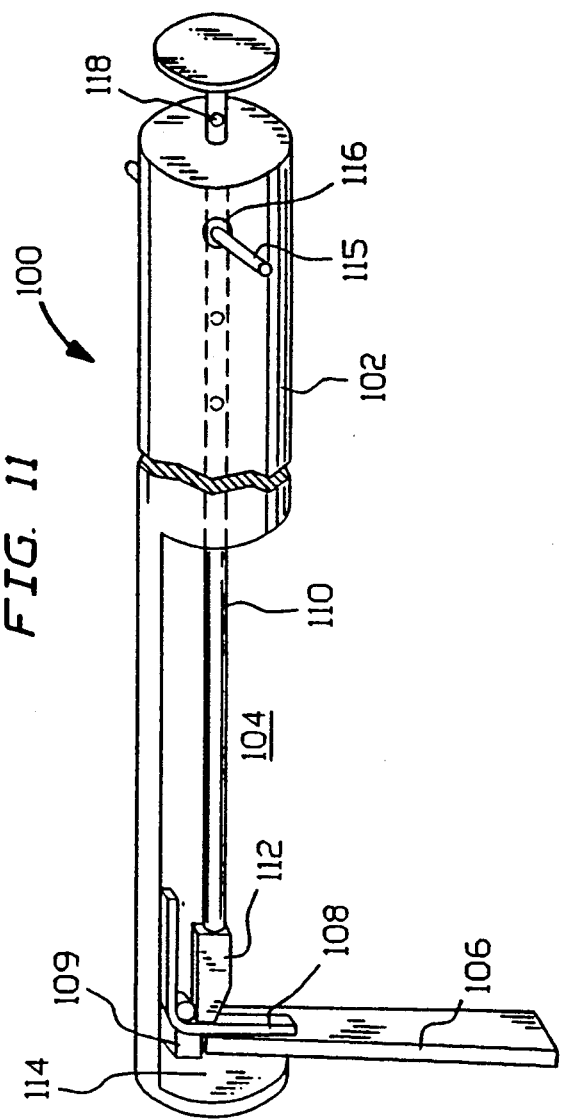

SPREADABLE LAPAROSCOPIC RETRACTOR AND ASSOCIATED METHOD OF USE

CROSS-REFERENCE TO A RELATED APPLICATION

This application is a continuation-in-part of commonly owned application Ser. No. 792,379 filed Nov. 15, 1991, now U.S. Pat. No. 5,152,279.

BACKGROUND OF THE INVENTION

This invention relates to a surgical instrument. More particularly, this invention relates to a retractor for use in laparoscopic surgery. This invention also relates to an associated surgical method.

In laparoscopic surgery, one or more openings are made in a patient's abdominal wall, usually by piercing the wall with the aid of a trocar. A laparoscope is inserted through one of the openings to enable a surgeon to see organs and tissues which are located in the patient's abdominal cavity. Usually, operating instruments such as grasping forceps and cutting tools are inserted into the abdominal cavity through ancillary openings made in the abdominal wall.

Some internal organs or tissues are disposed under other organs when the patient is lying on his or her back (the normal posture during laparoscopic surgery). The overlying organs must be lifted or otherwise displaced prior to operating on the underlying organs. Generally, a grasping forceps is used to grip an overlying organ and pull it upwardly to provide access to the desired surgical site. This procedure is frequently cumbersome, if not ineffective, to adequately expose the underlying organs and tissues.

OBJECTS OF THE INVENTION

An object of the present invention is to provide an improved technique for temporarily displacing an internal body organ of a patient during laparoscopic surgery.

Another object of the present invention is to provide an associated surgical instrument for use in laparoscopic surgery.

Another, more particular, object of the present invention is to provide a laparoscopic surgical retractor.

A further particular object of the present invention is to provide such a retractor which is easy to use and inexpensive to fabricate.

SUMMARY OF THE INVENTION

A retractor instrument for use in laparoscopic surgery comprises, in accordance with the present invention, an elongate frame member having a proximal end and a distal end and a retractor member having a pair of opposite ends, the retractor member being pivotably mounted to the frame member at a point spaced from the proximal end thereof. The retractor instrument further comprises a tube slidably surrounding at least a portion of the frame member and at least a portion of the retractor member in an insertion configuration of the retractor instrument, whereby the retractor member is held in substantially parallel relation to the frame member during an insertion of the retractor instrument through a patient's abdominal wall and partially into the patient's abdominal cavity in a laparoscopic procedure. The retractor member is pivotably mounted to the frame member at a point on the retractor member spaced from both of the opposite ends, whereby, upon a pivoting of the retractor member away from the frame member, the tube may be brought into contact with the retractor member to maintain the retractor member in an angled orientation with respect to the frame member during utilization of the retractor instrument to displace an internal body organ of the patient in the laparoscopic procedure.

According to additional features of the present invention, the retractor member comprises a plurality of rods pivotably attached to a bracket member, while a spreader or separator is operatively connected to the rods for spreading the rods away from one another to effectively enlarge the retractor member. The separator may comprise a slider member slidably coupled to the rods and further comprise a tensile member connected to the slider member for drawing the slider member along the rods.

Pursuant to another feature of the present invention, a locking mechanism or component is provided for locking the frame member relative to the tube upon a bringing of the tube into contact with the retractor member to maintain the angled orientation thereof.

A retractor instrument for use in laparoscopic surgery comprises, in accordance with another conceptualization of the present invention, an elongate frame member having a proximal end and a distal end and a plurality of elongate rods each pivotably fastened to the frame member at a distal end thereof. A separator is operatively connected to the rods for spreading the rods from a relatively close configuration to a spread-out configuration substantially defining a plane.

A method for use in laparoscopic surgery comprises, in accordance with the present invention, the steps of (i) providing a retractor instrument comprising an elongate frame member and a retractor member movably mounted to the frame member, (ii) holding the frame member and the retractor member in parallel relation to one another by means of a tube at least partially surrounding the frame member and the retractor member, (iii) inserting the frame member, the retractor member and the tube partially through an opening in a patient's abdominal wall, while maintaining the tube about the frame member and the retractor member, and (iv) upon a partial insertion of the retractor instrument into an abdominal cavity of the patient, sliding the tube and the frame member relative to one another to free the retractor member so that the retractor member is angled with respect to the frame member. Subsequent steps of the laparoscopic surgical method include (v) manipulating the frame member so that the retractor member engages a selected internal body organ of the patient, and (vi) during the step of manipulating, maintaining the tube in a fixed position relative to the frame member to maintain the retractor member in a predetermined orientation with respect to the frame member. Upon engaging the selected internal body organ with the retractor member, a force is exerted on the frame member. The retractor member is maintained in an angled orientation with respect to the frame member during the exertion of the force, whereby the position of the selected internal body organ in the abdominal cavity of the patient is shifted.

Where the retractor member is pivotably attached to the frame member, the retractor member pivots under the force of gravity upon a sliding of the tube in step (iv) above.

In accordance with another feature of the present invention, the laparoscopic surgical method further comprises the steps of moving the retractor instrument to disengage the retractor member and the selected internal body organ of the patient and, upon a disengagement of the retractor member and the internal body organ, manipulating the retractor instrument to shift the retractor member so that the retractor member is again substantially parallel with respect to the frame member. The frame member and the retractor member are then withdrawn from the abdominal cavity of the patient through the opening while maintaining the retractor member and the frame member in substantially parallel relation with respect to one another.

The present invention provides an improved technique for temporarily displacing an internal body organ of a patient during laparoscopic surgery. A surgical instrument in accordance with the present invention is an effective laparoscopic retractor. It is easy to use and inexpensive to fabricate.

BRIEF DESCRIPTION OF THE DRAWING

FIG. 1 is a schematic longitudinal cross-sectional view of a retractor for use in laparoscopic surgery, showing a retractor member in a closed or storage configuration.

FIG. 2 is a schematic longitudinal cross-sectional view similar to FIG. 1, showing the retractor member of that drawing figure in an opened or use configuration.

FIG. 3 is a schematic perspective view of another laparoscopic retractor, showing a pair of retractor members in an opened or use configuration.

FIG. 6 is a schematic side perspective view of yet another laparoscopic retractor.

FIG. 8 is partially a perspective view and partially a side elevational view of a further laparoscopic retractor, showing a retractor member in a closed or storage configuration.

FIG. 9 is a view similar to FIG. 8, showing the retractor member of that figure in an opened or use orientation.

FIG. 10 is a perspective view of yet another laparoscopic retractor, showing a retractor member in a closed or storage orientation with respect to a frame member.

FIG. 11 is a view similar to FIG. 10, showing the retractor member of that figure in an opened orientation extending orthogonally with respect to the frame member.

DETAILED DESCRIPTION

Figure 4:
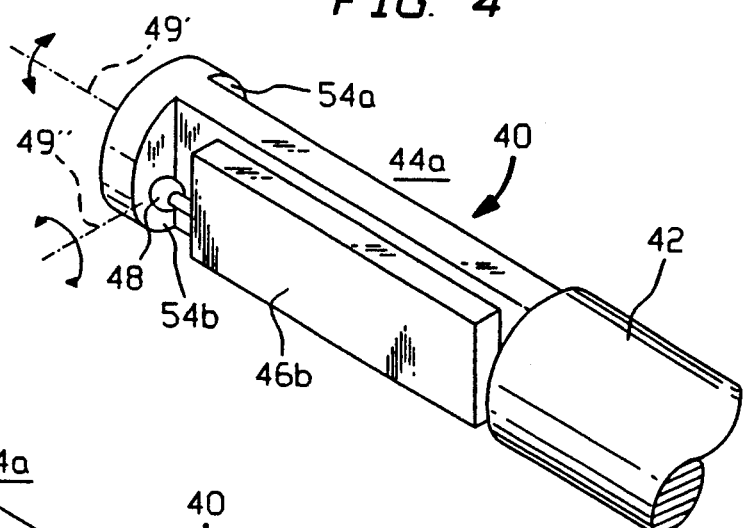
FIG. 4 is a partial perspective view, from a different angle, of the laparoscopic retractor of FIG. 3, showing the retractor members in a closed or storage configuration.

As illustrated in FIGS. 1 and 2, a retractor 20 for use in laparoscopic surgery comprises a substantially rigid frame or body member 22 provided at a distal end with an elongate recess 24 for receiving a substantially rigid retractor arm 26 in a retracted, storage configuration. Retractor arm 26 is swingably mounted to frame or body member 22 at a pivot pin 28. During insertion of the laparoscopic retractor 20 through an opening formed in a patient's abdominal wall (more specifically, through a tubular member traversing the abdominal wall), retractor arm 26 is held in recess 24, in a substantially parallel orientation with respect to frame 22, by a slider element 30. Upon sufficient insertion of the distal end of retractor 20 into the abdominal cavity of the patient, slider 30 is grasped and pulled in a proximal direction via a finger ring 32 or other manual actuator part. The opening of recess 24 due to the sliding away of slider 30 frees retractor arm 26 to swing about pivot pin 28 under the force of gravity, whereby the retractor arm assumes an opened or use configuration shown in FIG. 2.

During a laparoscopic surgical procedure using laparoscopic retractor 20 of FIGS. 1 and 2, an opening is formed in a patient's abdominal wall, for example, through the use of a trocar. A tubular member is inserted through the opening in a conventional technique for maintaining the opening in a dilated state. Upon insertion of frame 22 and retractor arm 26 in the closed, mutually parallel configuration of FIG. 1 through the abdominal opening, slider 30 is shifted in the proximal direction to enable retractor arm 26 to rotate downwardly so that the retractor arm is angled essentially orthogonally with respect to frame 22, as shown in FIG. 2. Frame 22 is then manipulated so that retractor arm 26 engages a selected internal body organ of the patient, such as the liver. Upon engaging the selected internal body organ with retractor arm 26, the operating surgeon or attendant pulls on frame 22 to displace or shift the liver into an at least partially retracted position. During this retraction of the selected internal body organ, retractor arm 26 is maintained in an essentially orthogonal orientation with respect to frame 22 by virtue of an arrest or stop 34 on frame 22, which prevents or blocks further rotation of retractor arm 26.

Upon the completion of a laparoscopic surgical operation on an organ or tissues underlying the retracted organ, frame 22 is moved to disengage retractor arm 26 and the retracted internal body organ of the patient. Upon completing the disengagement of the retractor arm 26 and the internal body organ, the surgeon or attendant rotates retractor instrument 20 so that retractor arm 26 pivots in a reverse direction about pivot pin 28 and again assumes the substantially parallel configuration of FIG. 1. Slider 30 is then shifted in the distal direction to lock retractor arm 26 in recess 24. Frame 22 and retractor arm 26 are then withdrawn from the patient through the abdominal opening.

It is to be noted that it is not necessary for slider 30 to completely close recess 24 in order to lock retractor arm 26 in the closed or parallel configuration of FIG. 1.

In fact, slider 30 need only overlap the proximal tip of retractor arm 26. It is to be further noted that retractor arm 26 may be maintained in parallel with respect to frame 22 solely by gravity. In that case, slider 30 may be omitted. During an insertion step of a laparoscopic procedure utilizing such a modified retractor instrument, the frame or body member is held to keep the retractor arm on the upper side. Upon sufficient insertion of the retractor instrument into the patient's abdominal cavity, the frame is rotated to allow the retractor arm to pivot downwardly under the force of gravity.

Figure 5:
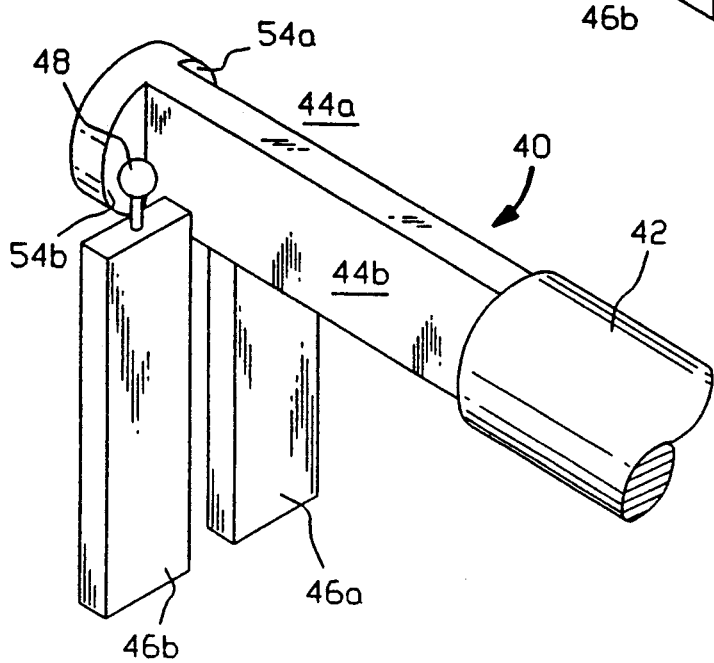
FIG. 5 is a partial perspective view similar to FIG. 4, showing the retractor members in the opened configuration of FIG. 3.

As illustrated in FIGS. 3-5, another retractor instrument 40 comprises an elongate, essentially tubular, frame or body member 42 to a distal end 43 of which a pair of substantially rigid planar retractor arms 46a and 46b are pivotably secured. As shown in FIG. 4, retractor arms 46a and 46b are held in parallel planes in respective recesses or chambers 44a and 44b by respective locking elements 50a and 50b (FIG. 3) which are slidably mounted to frame 42. Retractor arms 46a and 46b are pivotably attached to the distal end 43 of frame 42 via respective universal couplings 48 (only one shown in the drawings). Universal couplings 48 permit retractor arms 46a and 46b to pivot about two axes 49' and 49" (FIG. 4) upon a proximally directed stroke of locking elements 50a and 50b. Such a stroke of locking elements 50a and 50b opens recesses 44a and 44b and enables retractor arms 46a and 46b to fall under the force of gravity into the essentially orthogonal orientation of FIGS. 3 and 5 wherein arms 46a and 46b are in essentially the same plane. During use of retractor instrument 40 to retract an organ such as the liver, retractor arms 46a and 46b are maintained in their common plane essentially perpendicular to frame 42 by arresting surfaces 54a and 54b at the distal end 43 of frame 42.

It is to be noted that retractor instrument 20 of FIGS. 1 and 2 may be modified to assume specific design features of the embodiment of FIGS. 3-5. For example, retractor arm 26 may be pivotably connected to frame 22 via a universal type coupling. In addition, slider 30 may have an arcuate cross-section like locking elements 50a and 50b, rather than a rectangular cross section.

Similarly, retractor instrument 40 of FIGS. 3-5 may be altered to take on specific design elements shown in the embodiment of FIGS. 1 and 2. For example, retractor instrument 40 might have one integral locking element instead of two separate ones.

Figure 7A:
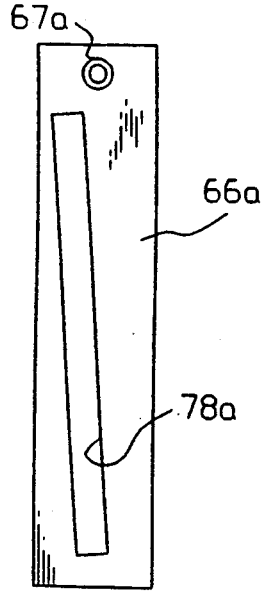
FIGS. 7A-7C are elevational views of three cooperating retractor members shown in FIG. 6.
Figure 7B:
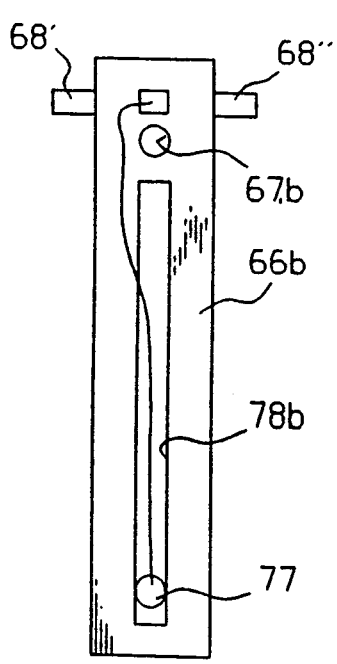
Figure 7C:
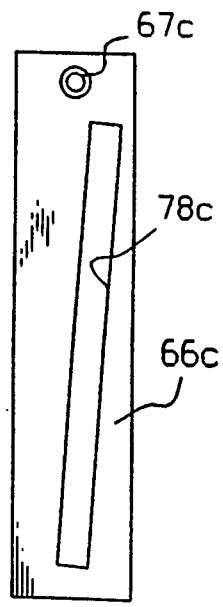

FIGS. 6 and 7A-7C illustrate a further retractor instrument 60. Retractor instrument 60 is provided with three overlapping or interleaved retractor arms 66a, 66b, and 66c. Retractor arms 66a, 66b, and 66c are pivotably mounted to a distal end 63 of a frame or body member 62 via one or two pivot pins 68' and 68" on center retractor arm 66b. Retractor arms 66a, 66b, and 66c are held or locked in a recess or chamber 64 in frame 62 by a cross-sectionally arcuate slider element 70. Outer retractor arms 66a and 66c are pivotably mounted for rotating outwardly in opposite directions in the manner of a fan so that all three retractor arms 66a, 66b, 66c assume a triangular use configuration, as depicted in FIG. 6. Retractor arms 66a and 66c are pivotably connected to retractor arm 66b via mating lugs 67a and 67c which traverse a bore 67b in retractor arm 66b (FIGS. 7A-7C).

It is to be noted that retractor arms or plates 66a and 66c may be pivotably connected to center retractor arm 66b at a point above pivot pins 68' and 68", rather than below the pivot pins, as illustrated in FIGS. 6 and 7A-7C. Alternatively, retractor arms 66a and 66c may be pivotably connected directly to frame 62 via respective universal type couplings (not shown).

To implement the swinging of retractor arms 66a and 66c about an axis 71 extending substantially parallel to frame 62, a wire 75 extends from a finger ring 76 at a proximal end of frame 62 to a pin or peg 77 which traverses camming slots 78a, 78b, and 78c in retractor arms 66a, 66b, and 66c, respectively. Slot 78b extends centrally with respect to center retractor arm 66b, while slots 78a and 78c are inclined with respect to outer retractor arms 66a and 66c. Cable is initially shifted in the distal direction so that peg 77 is located near the free ends of retractor arms 66a, 66b, and 66c while the arms are disposed in a stacked parallel configuration inside recess 64. After slider 70 has been shifted in the proximal direction and after retractor arms 66a, 66b, and 66c have fallen into an orthogonal orientation, wire 75 is pulled in the proximal direction to spread arms 66a, 66b, and 66c. After a laparoscopic surgical operation utilizing retractor instrument 60 is completed, frame 62 is shaken or vibrated to allow peg 77 to fall to the bottoms of slots 78a, 78b, and 78c. Frame 62 is then rotated to swing retractor arms 66a, 66b, and 66c back into the storage position inside recess 64. Slider 70 is then shifted in the distal direction to lock the retractor arms in the closed, storage position and the retractor instrument is withdrawn from the abdominal cavity of the patient.

As shown in FIGS. 8 and 9, an additional retractor instrument 80 comprises a frame or body member 82 defining a recess 84 in which a retractor arm 86 is disposed during a storage or insertion phase of a laparoscopic procedure. A leaf spring 88 is prestressed or biased to maintain retractor arm 86 in recess 84 in a parallel orientation with respect to body member 82, as illustrated in FIG. 8. Leaf spring 88 extends around a lug or rod element 89 and is connected to a cable 90. Upon a pulling of cable 90 via a finger ring 92 attached thereto, leaf spring 88 partially straightens out owing to its being forced along rod element 89, and thereby rotates retractor arm 86 into an essentially orthogonal orientation shown in FIG. 9. The further unbending of leaf spring 88 and the further concomitant rotation of retractor arm 86 is stopped by an arresting surface 94 at the distal end of body member 82. A locking element in the form of a plug 95 bearing at one end two opposing fingers 96a and 96b is connected to cable 90 for locking the cable during a retraction operation. During a withdrawing stoke of cable 90, plug 95 with fingers 96a and 96b passes through an aperture 97 with finger-like extensions 98a and 98b at a proximal end of body member 82. Upon the passage of fingers 96a and 96b outside of body member 82, plug 95 is twisted to angularly displace fingers 96a and 96b with respect to extensions 98a and 9b, thereby locking cable 90 in a fixed position in opposition to the restoring force provided by the spring bias of leaf spring 88. The above-described process is reversed to close retractor instrument 80.

FIGS. 10 and 11 illustrate yet another retractor instrument 100 which comprises a frame or body member 102 defining a recess 104 in which a retractor arm 106 is disposed during a storage or insertion phase of a laparoscopic procedure. A leaf spring 108 is prestressed or biased to maintain retractor arm 106 in recess 104 in a parallel orientation with respect to body member 102, as illustrated in FIG. 10. Leaf spring 108 is fixed to frame member 102 at 109. A push rod 110 provided at a distal end with a wedge 112 is slidably mounted to frame 102. During a retractor opening step, leaf spring 108 is partially straightened out by wedge 112 in response to a distally directed stroke of push rod 110. Retractor arm 106 is thereby rotated into an essentially orthogonal orientation shown in FIG. 11. Further unbending of leaf spring 108 and further concomitant rotation of retractor arm 106 is stopped by an arresting surface 114 at the distal end of body member 102. A locking element in the form of a pin 115 is inserted through openings 116 (only one visible in the drawing) in frame 102 and through an aligned opening in an array of openings 118 in push rod 110, to maintain retractor arm 106 in the opened configuration shown in FIG. 11.

As illustrated in FIGS. 12A-12D, a laparoscopic retractor comprises a tubular outer member 120 in which an elongate rod or frame member 122 is slidably inserted. Rod 122 is provided at a proximal end with a flange 124 for facilitating manual sliding of the rod relative to tubular member 120 and is further provided at a distal end with a substantially planar retractor member 126 pivotably attached to rod 122 at pivot point 128. Pivot point 128 is spaced from each end of retractor member 126.

Figure 12A:
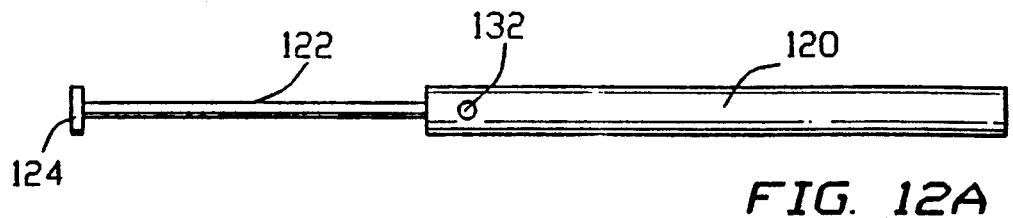
FIGS. 12A-12D are schematic side elevational views of a laparoscopic retractor in accordance with the present invention, showing different steps in the utilization of the retractor.

During an initial step of a laparoscopic retracting procedure, illustrated in FIG. 12A, rod 122 is maintained in a proximal disposition relative to tubular member 120 so that retractor member 126 is at least partially withdrawn into tubular member 120. This relative configuration of components 120, 122 and 126 ensures that retractor member 126 is locked in a position extending essentially parallel to rod 122.

Figure 12B:
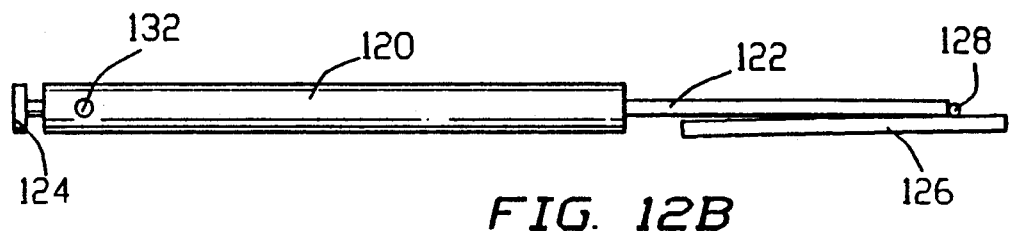
Figure 12C:
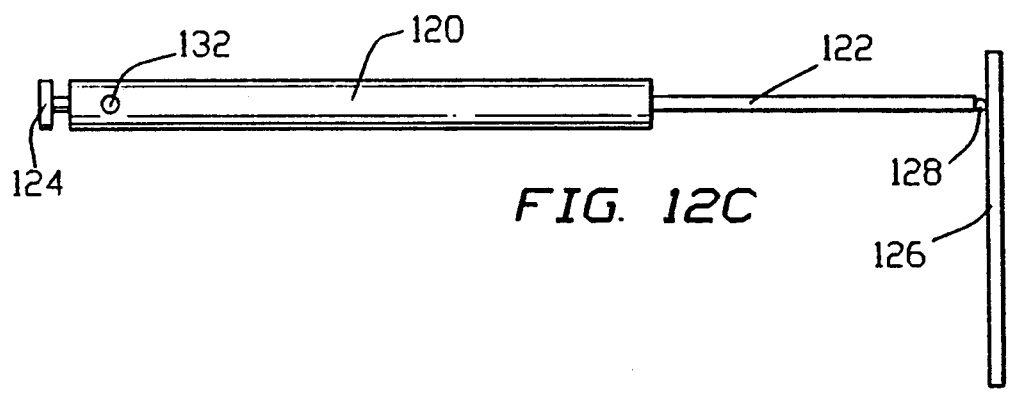

Upon an insertion of tubular member 120 through a patient's abdominal wall (not shown) so that a distal portion of the tubular member projects into the abdominal cavity, rod 122 is pushed in the distal direction so that retractor member 126 come completely out of tubular member 120, as illustrated in FIG. 12B. At that point, retractor member 126 swings downwardly about pivot point 128 under the action of gravity, as depicted in FIG. 12C. It may be necessary to rotate rod 122 about its longitudinal axis (not designated) in order to enable the pivoting of retractor member 126.

Figure 12D:
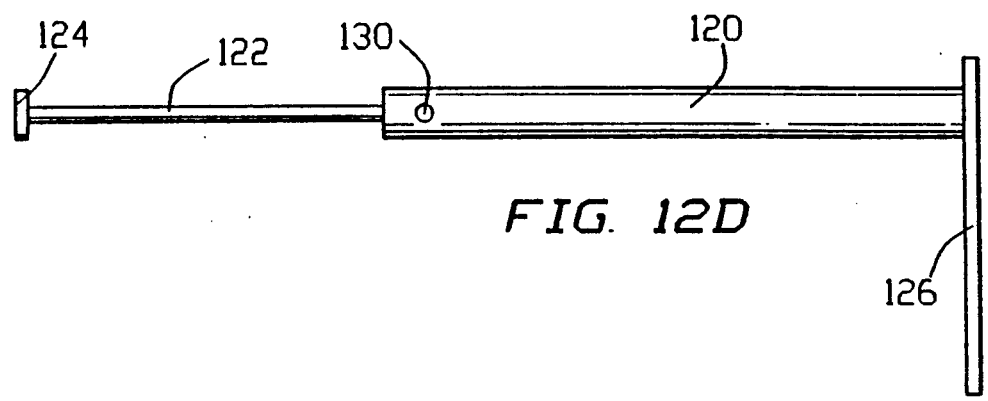

Upon the swinging of retractor member 126 into the lowered or extended position of FIG. 12C, rod 122 is pulled back in the proximal direction relative to tubular member 120, thereby bringing retractor member 126 into a locking engagement with a distal edge or end of tubular member 120, as shown in FIG. 12D. A pin 130 may be inserted through a hole 132 (FIGS. 12A-12C) in tubular member 120 to temporarily lock rod 122 to tubular member 120. It is to be noted that retractor member 126 and tubular member 120 or rod 122 together form a substantially L-shaped use configuration wherein retractor member 126 extends substantially perpendicularly with respect to tubular member 120 and rod 122. Upon an exerting of force on rod 122 and tubular outer member 120, retractor member 126 may be used to pull or push an internal body organ of a patient, to permit access to underlying organs or tissues.

Figure 13A:
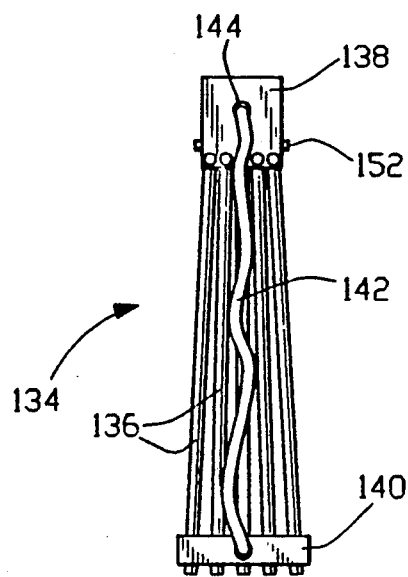
FIGS. 13A and 13B are schematic front elevational views of a spreadable retractor member in accordance with the present invention, showing different steps in the utilization of the retractor member.
Figure 13B:
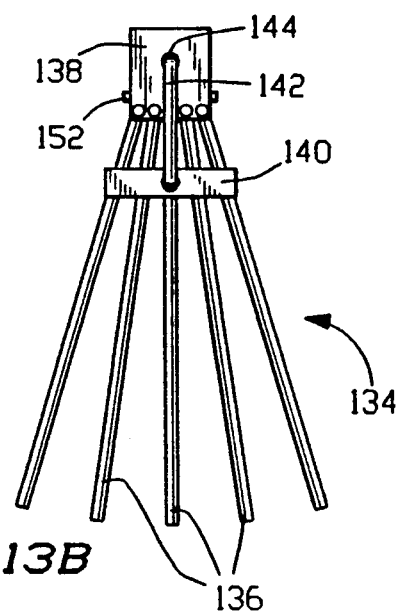

As illustrated in FIGS. 13A and 13B, a retractor member 134 of a laparoscopic type retractor shown in FIGS. 14A-14E comprises a plurality of rods 136 each pivotably attached at one end to a bracket or base 138. Rods 136 traverse respective bores (not shown) in a relatively massive slider member 140. A wire 142 traverses an opening 144 in bracket 138 and is connected at one end to slider member 140. Upon a placement of tension on wire 142, slider member 140 slides along rods 136 from free ends thereof towards bracket 138, thereby spreading rods 136 in the manner of a hand-held fan and adjusting retractor member 134 from a pre-use configuration shown in FIG. 13A to a spread use configuration shown in FIG. 13B.

As illustrated in FIGS. 14A-14E, a laparoscopic retractor incorporating retractor member 134 comprises a tubular outer member 146 in which an elongate frame member or shaft 148 is slidably inserted. Shaft 148 is provided at a proximal end with a flange 150 for facilitating manual sliding of the shaft relative to tubular member 146 and is further provided at a distal end with retractor member 134. Bracket 138 of retractor member 134 is pivotably attached to shaft 148 at pivot elements 152. Pivot elements 152 define a pivot axis (not shown) spaced from each end of retractor member 134.

Figure 14A:
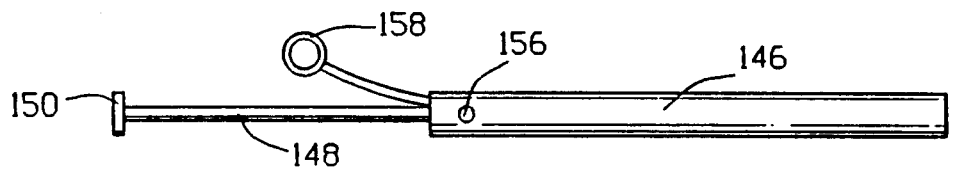
FIGS. 14A-14E are schematic side elevational views of a laparoscopic retractor incorporating the retractor member shown in FIGS. 13A and 13B, showing successive stages in the utilization of the retractor.

During an initial step of a laparoscopic retracting procedure, illustrated in FIG. 14A, shaft 148 is maintained in a proximal disposition relative to tubular member 146 so that retractor member 134 is at least partially withdrawn into tubular member 146. This relative configuration of components 146, 148, and 134 ensures that retractor member 134 is locked in a position extending essentially parallel to shaft 148 and tubular member 146.

Figure 14B:
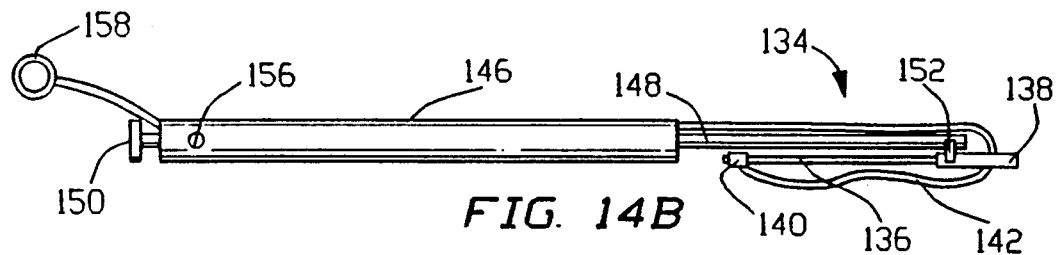
Figure 14C:
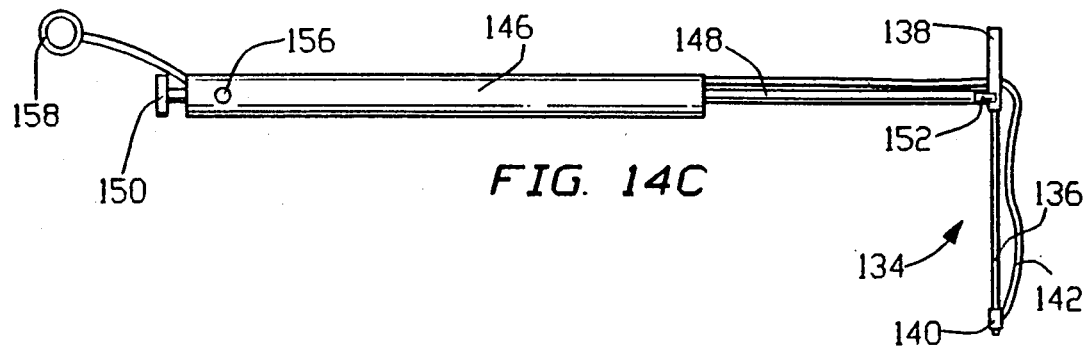

Upon an insertion of tubular member 146 through a patient's abdominal wall (not shown) so that a distal portion of the tubular member projects into the abdominal cavity, shaft 148 and tubular member 146 are shifted relative to one another so that retractor member 134 comes completely out of tubular member 146, as illustrated in FIG. 14B. At that point, retractor member 134 swings downwardly about pivot elements 152 under the action of gravity, as depicted in FIG. 14C. It may be necessary to rotate shaft 148 about its longitudinal axis (not shown) in order to enable the pivoting of retractor member 134.

Figure 14D:
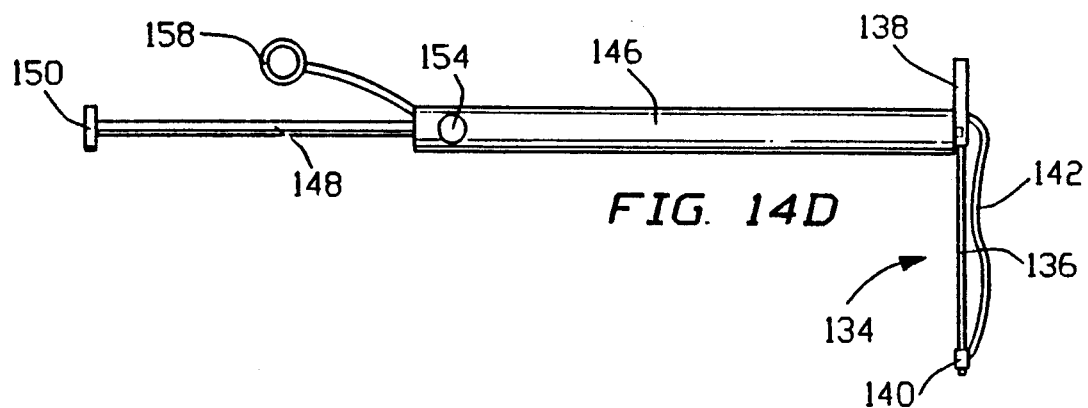
Figure 14E:
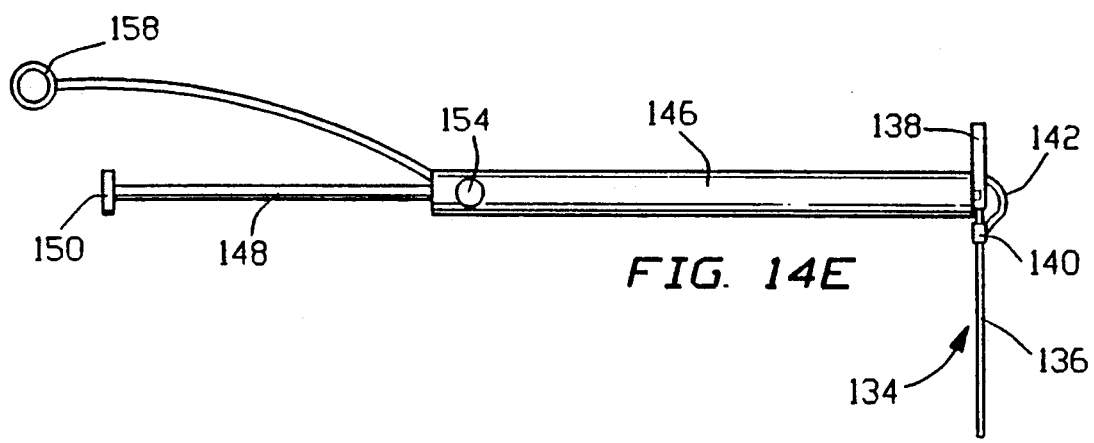

Upon the swinging of retractor member 134 into the lowered or extended position of FIG. 14C, shaft 148 and tubular member 146 are shifted relative to one another to bring bracket 138 into a locking engagement with a distal edge or end of tubular member 146, as shown in FIG. 14D, at opposite sides of pivot elements 152. A pin 154 may be inserted through a hole 156 (FIGS. 14A-14C) in tubular member 146 to temporarily lock shaft 148 to tubular member 146. It is to be noted that retractor member 134 and tubular member 146 or shaft 148 together form a substantially L-shaped use configuration wherein rods 136 extend substantially perpendicularly with respect to tubular member 146 and shaft 148.

Wire 142 extends from slider member 140 through opening 144 and tubular outer member 146 to a ring 158 disposed at the proximal end of the tubular outer member. Upon the pulling of retractor member 134 in the proximal direction so that bracket 138 is locked against the distal end of tubular outer member 146, as illustrated in FIG. 14D, a surgeon or other operator pulls on wire 142 via ring 158, thereby shifting slider member 140 upwardly along rods 136 towards bracket 138, to spread rods 136 into the configuration of FIG. 13B. Retractor member 134 may now be used to pull or push a relatively large internal body organ of a patient, to permit access to underlying organs or tissues.

To withdraw the retractor of FIGS. 14A-14E upon the termination of a retraction procedure, the tension on wire 142 is relaxed (a lock may be provided to maintain that tension during the operation), whereupon slider member falls to the lower ends of rods 136, drawing the rods together into the configuration of FIG. 13A. Shaft 148 may then be turned about its longitudinal axis to cause rods 136 and slider member 140 to collapse back upon shaft 148. Shaft 148 is then pulled in the proximal direction relative to tubular member 146, thereby withdrawing retractor member 134 into tubular member 146.

Figure 15A:
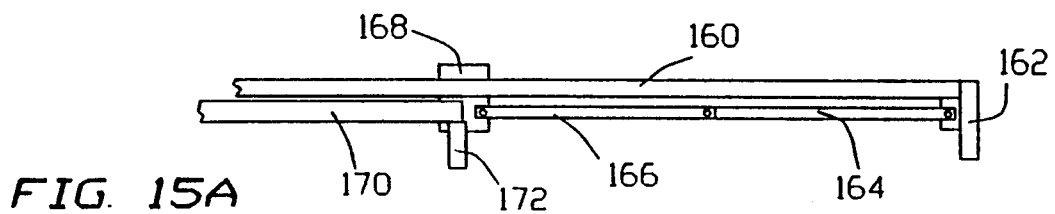
FIGS. 15A and 15B are schematic side elevational views of another laparoscopic retractor in accordance with the present invention, showing a pre-use or insertion configuration and a use or extended configuration.
Figure 15B:
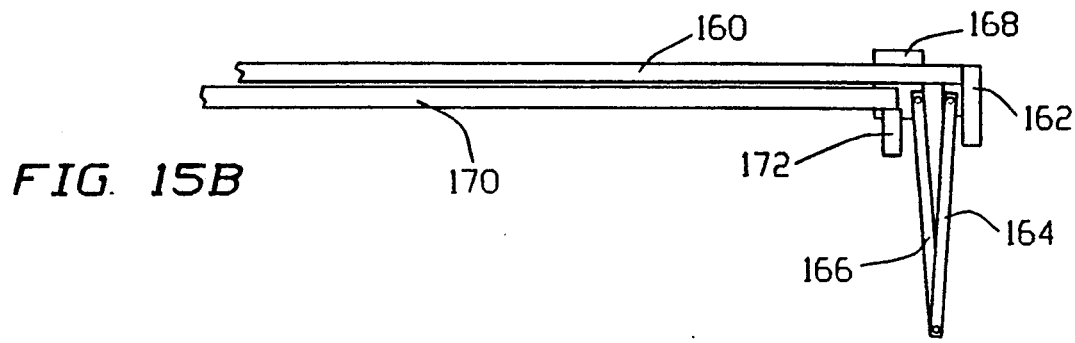

As depicted in FIGS. 15A and 15B, another retractor for use particularly in laparoscopic surgery comprises an elongate body member 160 having a flange 162 at a distal end. A first retractor member 164 is pivotably attached at a distal end to body member 160 and is pivotably attached at a proximal end to a second retractor member 166. A proximal end of retractor member 166 is pivotably connected to a slider member 168 which is slidably fastened to body member 160. Slider member 168 is connected to the distal end of a push-pull rod 170 and carries a flange or stop 172. Upon a pushing of rod 170 in the distal direction, retractor members 164 and 166 fold outwardly, as shown in FIG. 15B. Flanges or stops 162 and 172 limit swinging of retractor members 164 and 166 during a retraction operation. Flanges or stops 162 and 172 may be omitted, insofar as the different points of connection of retractor members 164 and 166 to body member 160 limit the rotation the two members can undergo.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are offered, by way of example to facilitate comprehension of the invention and should not be construed to limit the scope thereof.

What is claimed is:

1. A retractor instrument for use in laparoscopic surgery, comprising:
    an elongate frame member having a proximal end and a distal end;
    a retractor member having a pair of opposite ends, said retractor member being pivotably mounted to said frame member at a point spaced from said proximal end of said frame member and also spaced from both of said opposite ends of said retractor member, said retractor member extending at a predetermined angle with respect to said frame member; and
    a tube slidably surrounding a portion of said frame member, said tube having a distal edge in engagement with said retractor member on opposite sides of said point, whereby said retractor member is maintained in said predetermined angle with respect to said frame member during utilization of the retractor instrument to displace an internal body organ of the patient in the laparoscopic procedure.

2. The instrument defined in claim 1 wherein said retractor member comprises a plurality of rods pivotably attached to a bracket member.

3. The instrument defined in claim 2, further comprising means operatively connected to said rods for spreading said rods away from one another to effectively enlarge said retractor member.

4. The instrument defined in claim 3 wherein said means for spreading comprises a slider member slidably coupled to said rods and further comprises a tensile member connected to said slider member for drawing same among said rods.

5. The instrument defined in claim 1, further comprising locking means for locking said frame member relative to said tube upon a bringing of said tube into contact with said retractor member in said angled orientation.

6. A retractor instrument for use in laparoscopic surgery, comprising:
    an elongate frame member having a proximal end and a distal end;
    a plurality of elongate rods each pivotably fastened to said frame member at a distal end thereof for motion between an insertion configuration in which all of said rods are parallel to said frame member and a use configuration wherein all of said rods are disposed in essentially a single plane, said plane extending at an angle with respect to said frame member; and
    separator means operatively connected to said rods for spreading same from a relatively close configuration to a spread-out configuration substantially defining said plane.

7. The instrument defined in claim 6 wherein said separator means comprises a slider member slidably coupled to said rods and further comprises a tensile member connected to said slider member for drawing same along said rods.

8. The instrument defined in claim 7, further comprising a tube slidably surrounding a least a portion of said frame member and at least a portion of each of said rods in an insertion configuration of the retractor instrument, whereby said rods are held in substantially parallel relation to said frame member during an insertion of the retractor instrument through a patient's abdominal wall and partially into the patient's abdominal cavity in a laparoscopic procedure.

9. A method for use in laparoscopic surgery, comprising the steps of:
    (a) providing a retractor instrument comprising an elongate frame member and a retractor member pivotably mounted to said frame member, said retractor instrument further comprising a tube in which said frame member is slidably mounted;
    (b) holding at least portions of said frame member and said retractor member inside said tube so that said tube maintains said frame member and said retractor member in parallel relation to one another;
    (c) during said step of holding, inserting said frame member, said retractor member and said tube partially through an opening in a patient's abdominal wall;
    (d) upon a partial insertion of the retractor instrument into an abdominal cavity of the patient, sliding said tube relative to said frame member and said retractor member to move said retractor member completely out from said tube so that said retractor member can be angled with respect to said frame member;
    (e) shifting said frame member in the proximal direction relative to said tube so that said retractor member is brought into engagement with opposing distal edges of said tube, thereby maintaining said retractor member in a predetermined orientation relative to said frame member;
    (f) manipulating said frame member so that said retractor member engages a selected internal body organ of the patient;

(g) during said step of manipulating, maintaining said distal edge of said tube in engagement with said retractor member to hold said retractor member in said predetermined orientation with respect to said frame member;
(h) upon engaging the selected internal body organ with said retractor member, exerting a force on said frame member; and
(i) maintaining said retractor member in an angled orientation with respect to said frame member during said step of exerting, whereby the position of the selected internal body organ in the abdominal cavity of the patient is shifted.

10. The method set forth in claim 9 wherein said retractor member is pivotably attached to said frame member, said retractor member pivoting under the force of gravity upon a sliding of the tube in step (d).

11. The method set forth in claim 10, further comprising the steps of:
(i) moving the retractor instrument to disengage said retractor member and the selected internal body organ of the patient;
(j) upon a disengagement of the retractor member and the internal body organ, manipulating the retractor instrument to shift aid retractor member so that said retractor member is again substantially parallel with respect to said frame member; and
(k) withdrawing said frame member and said retractor member from the abdominal cavity of the patient through said opening while maintaining said retractor member and said frame member in substantially parallel relation with respect to one another.

* * * * *